(12) United States Patent
Scipolo et al.

(10) Patent No.: US 11,921,036 B2
(45) Date of Patent: Mar. 5, 2024

(54) IN SITU APPARATUS FOR FURNACE OFF-GAS CONSTITUENT AND FLOW VELOCITY MEASUREMENT

(71) Applicant: TENOVA GOODFELLOW INC., Mississauga (CA)

(72) Inventors: Vittorio Scipolo, Etobicoke (CA); Avishekh Pal, Toronto (CA)

(*) Notice: Subject to any disclaimer, the term of this patent is extended or adjusted under 35 U.S.C. 154(b) by 557 days.

(21) Appl. No.: 17/271,732

(22) PCT Filed: Sep. 9, 2019

(86) PCT No.: PCT/CA2019/000126
§ 371 (c)(1),
(2) Date: Feb. 26, 2021

(87) PCT Pub. No.: WO2020/056485
PCT Pub. Date: Mar. 26, 2020

(65) Prior Publication Data
US 2021/0318233 A1    Oct. 14, 2021

Related U.S. Application Data

(60) Provisional application No. 62/734,345, filed on Sep. 21, 2018.

(51) Int. Cl.
*G01N 21/31* (2006.01)
*F27B 3/28* (2006.01)
(Continued)

(52) U.S. Cl.
CPC ........... *G01N 21/3103* (2013.01); *F27B 3/28* (2013.01); *F27D 21/00* (2013.01); *G01N 33/004* (2013.01);
(Continued)

(58) Field of Classification Search
None
See application file for complete search history.

(56) References Cited

U.S. PATENT DOCUMENTS

| 6,271,522 B1 | 8/2001 | Lindermeir |
| 8,551,209 B2 | 10/2013 | Chanda |
| 2011/0045422 A1* | 2/2011 | Tanca ..................... F23J 15/003 73/23.31 |

FOREIGN PATENT DOCUMENTS

| CA | 3112868 | 3/2020 |
| CN | 104391132 | 3/2015 |

(Continued)

OTHER PUBLICATIONS

Samuel Arnold, "Steelmaking Process Control Using Remote Ultraviolet Atomic Emission Spectroscopy", University of Toronto, 2015.

*Primary Examiner* — Harshad R Patel

(57) ABSTRACT

An optically based combustion off-gas stream velocity sensor assembly is provided for detecting in real-time off-gas flow velocity and/or volume as it moves through a flue duct. The sensor assembly includes two paired coherent light emitters and optic sensors, positioned in a spaced orientation in the flow path direction. The light emitter/optic sensor pairs operate to emit and detect across the off-gas stream coherent light beam energy having a wavelength component corresponding to an absorption profile of an off-gas species component. The detection of non-absorbed portions of the emitted beam is used to identify and detect the movement of a flow species signature at different locations along the flue duct.

29 Claims, 4 Drawing Sheets

(51) Int. Cl.
*F27D 21/00* (2006.01)
*G01N 33/00* (2006.01)
*G01P 5/22* (2006.01)

(52) U.S. Cl.
CPC ........ *G01P 5/22* (2013.01); *G01N 2201/0612* (2013.01)

(56) References Cited

FOREIGN PATENT DOCUMENTS

| | | |
|---|---|---|
| EP | 2 239 545 | 10/2010 |
| JP | 2009-168688 | 7/2009 |
| WO | WO 20128145829 A1 | 11/2012 |
| WO | PCT/CA2019/000126 | 3/2020 |

* cited by examiner

IN SITU APPARATUS FOR FURNACE OFF-GAS CONSTITUENT AND FLOW VELOCITY MEASUREMENT

RELATED APPLICATIONS

This application claims priority and the benefit of 35 USC 119(e) to U.S. Provisional Patent Application No. 62/734,345, filed 21 Sep. 2018, the entirety of which is incorporated herein by reference.

SCOPE OF THE INVENTION

The present invention relates to an apparatus and system for use in the real-time measurement of the off-gas flow properties from a combustion process. More particularly, an apparatus is provided which is operable for the in situ identification and/or measurement of one or more off-gas constituents or species of an off-gas stream, and which is used to measure or determine combustion off-gas flow velocities and/or volumes. The present invention preferably also provides an apparatus which is adapted to concurrently measure one or more off-gas flows, off-gas constituent concentrations and/or off-gas temperatures, and output signals to control combustion parameters in response thereto.

BACKGROUND OF THE INVENTION

The analysis of the individual gas species components of combustion process off-gases, such as those produced in steelmaking operations, may provide insight into the ongoing combustion process itself. It has been recognized that identifying and analyzing the specific types and combinations of individual off-gas species or components, may indicate to operators that adjustment of the combustion or furnace operating parameters or inputs may be needed for increased efficiencies or optimal furnace operation.

Various systems have been proposed for analyzing furnace combustion off-gasses. Typically, combustion gas analysers operate by propagating a light beam across part of an extracted sample of gas, and measuring the amount of light energy which is absorbed by a particular off-gas species component.

SUMMARY OF THE INVENTION

The applicant has appreciated that the velocity of the off-gas stream itself, or the velocity of particular gas species within the off-gas system may advantageously be used to provide real-time indication of combustion process parameters.

The present invention provides an apparatus for analysis of combustion off-gas flow velocity, and preferably flow velocity and/or volume which may be used to assess and/or optimize industrial furnace combustion processes, and which may include, for example, furnace operations of basic oxygen furnaces (BOFs) and electric arc furnaces (EAFs) used in steelmaking operations.

In one non-limiting embodiment, the present invention provides an apparatus for determining a velocity and/or a volume of a combustion gas flow, and most preferably, a combustion gas flow produced as off-gas of an industrial furnace such as a steelmaking or smelting furnace, a cement kiln, an industrial incinerator or the like. The present invention provides an off-gas velocity sensor assembly which is adapted to optically measure the velocity of the off-gas flow, or one or more individual off-gas species which is produced from the combustion process. Preferably the velocity in substantially real-time sensor assembly is used to determine the off-gas flow velocity as it moves through a portion of a vent stack, flue or duct (hereinafter collectively a duct). Further by providing part of the duct predetermined geometry, the volume output of the off-gas stream, and/or a particular lower component species thereof, may be determined.

The apparatus may be provided as part of an overall furnace control system, whereby data representing one or more of the sensed combustion off-gas velocity, volume and/or one or more off-gas flow species concentrations and/or temperatures for a furnace heat is compiled and compared with one or more control, predetermined or modeled heat profiles. Based on the difference between the sensed off-gas flow properties and the control or other predetermined or modeled furnace heat, furnace operating parameters, such as input volumes, combustion temperatures or furnace heat time, are adjusted to better optimize combustion operations or efficiencies and/or lower undesired emissions. The present system may also be used to control or monitor downstream scrubbers or other off-gas treatment systems, so that they are not overloaded and are optimized.

In another non-limiting embodiment, the off-gas velocity sensor assembly is provided as part of a furnace control system for an electric arc furnace (EAF) or basic oxygen furnace (BOF) used in steel processing. In the steelmaking furnace, input source materials such as iron containing scrap and a carbon source are introduced into a heating vessel together with oxygen during heating. During heating, the waste combustion gases which are formed are exhausted as an off-gas stream through a waste off-gas flue duct. In a simplified mounting orientation, the optical off-gas velocity sensor assembly is provided in the off-gas flue duct and is used to control the introduction of oxygen to optimize decarburization and/or the oxidation of slag.

The velocity sensor assembly may include two or more paired associated coherent light or other energy emitters and energy sensors operable to detect non-absorbed energy emitted by the associated energy emitter, and more preferably identify or detect gas species by absorption detection. Each pair of emitters and sensors is preferably arranged in the flue duct in a spaced orientation relative to each other, along the off-gas flow path direction. Preferably, each associated emitter/sensor pair is positioned to respectively emit and detect optically a coherent light beam which passes through part of the off-gas flow as it moves along a portion of the flue duct. Most preferably, the emitted coherent light beam includes wavelength energy which corresponds to an absorption energy profile of one or more off-gas species components.

Although not essential, each of the associated light emitter/optic sensor pairs are preferably positioned along a part of the off-gas flue duct which has a constant geometry; and in substantially the identical orientation and position relative to the cross-sectional geometry of the flue duct. In this positioning, the light emitter and sensor pairs operate to emit respective energy or coherent light beams across the substantially same portions of the off-gas flow. Different relative mounting orientation for individual emitter/sensor pairs may, however, also be used.

By detecting the non-absorbed portion of the emitted beam using the optic sensor, an absorption signature for the off-gas flow at a particular point in time may be generated. In a simplest embodiment, the absorption signature is determined as the total amount of energy absorbed across all wavelengths emitted or at one or more selected wavelength ranges. More preferably the optic sensor is operable to detect non-absorbed portions of the emitted beam energy at absorption wavelength frequencies for at least one preselected gas species for a particular portion of the moving off-gas stream at a point in time. The particular species concentrations determined by the absorption profiles and/or temperatures may be further used to generate the off-gas flow absorption signature. The applicant has recognized that by using multiple light emitter/sensor pairs to identify and detect a particular absorption signature, the time between such identification and detection at different physical points may be used to indicate the off-gas flow velocity.

Further by determining the flue duct geometry where optic sensing is performed, it is also possible, based on the detected flow velocity, to identify both the overall off-gas volume being emitted, as well as the volumes of one or more individual gas species. In another non-limiting embodiment, the sensor assembly may thus be used to monitor potential overloading of and/or effect control signals for downstream pollution control apparatus, such as chemical or gas scrubbers. In one possible non-limiting construction, each light emitter/sensor pair consists of a separate coherent light beam emitter, and preferably a tunable diode laser emitter, and an optical receptor or sensor. The emitter and sensor are adapted for separate placement, spaced from each other along generally opposite sides of a combustion off-gas flue duct. For increased accuracy, the light emitter/sensor pairs are preferably provided as a preassembly within a combined coherent light beam emitter/receptor head which is adapted to both emit and receive an emitted coherent light beam, and which are used respectively with one or more optic reflectors. The optic reflectors are positioned to retransmit coherent light beam energy which is emitted from the coherent light beam emitter head back through the off-gas stream to the receptor for increased beam travel path and accuracy. By sensing the non-absorbed portion of the reflected return beam energy, it is possible to provide data representative of total absorbed energy and/or concentration profiles of one or more gas flow species moving through the gas duct, and depending on the species, temperature of the off-gas flow.

In another non-limiting embodiment, to facilitate calibration, the light emitter/sensor pairs and/or the optic reflectors may be provided for mounting to the flue duct with a predetermined spacing, or as part of a modular optic emitter and/or optic reflector pre-assembly. Such a predetermined mounting arrangement may allow for simplified final positioning and calibration of the light emitter/sensor pairs along the off-gas flue duct.

In one possible construction, each light emitter/optic sensor pair is optically coupled to one or more photodetectors. The photodetectors are operable to generate and transmit to a computer, control processing unit (CPU), or processor (hereinafter collectively a processor), electric signals representative of the non-absorbed portion of the coherent light energy received and detected by each sensor. Preferably, the electric signals include signals representative of non-absorbed light energy, over at least one, and preferably a number of gas species absorption profiles, at each optic sensor.

In one non-limiting operational mode, the furnace control system is configured to identify and/or detect sensed coherent light beam energy at one or more specific absorption profiles for one or more selected target gas species. Preferably the system operates to identify absorption profiles for one or more of the off-gas species components $CH_4$, $H_2O$, $O_2$, $CO$ and/or $CO_2$ of the off-gas stream flowing through the flue duct. By selecting and outputting a coherent light beam or other energy beam with the correlated specific absorption profile of the one or more off-gas target species, the detected beam energy received at the optical sensors may be used to identify relative target gas species concentrations in a portion of off-gas flow at each optic sensor location. The processor further operates to correlate total absorbed energy and/or one or more of the detected target species concentrations with a particular gas absorption signature for the portion of the off-gas flow, and identify the time differences at which the gas absorption signature is detected at each associated light emitter/sensor pair. By determining the time sequence between the detection of the absorption signature, or specific species concentrations at each sensor, the system identifies and establishes time-of-flight of a particular portion of the off-gas stream as it moves along the flue duct between the light emitter/optic sensor pairs.

By inputting the flue geometry, and/or by the determined spacing between each associated emitter/optical sensor pair, the furnace control system may thus be used to calculate both target species flow velocity, the over combustion gas flow velocity, and by additionally calculating velocity and the known flue duct geometry, total combustion off-gas volume, and volume of one or more species components moving through the flue duct. Depending upon the determined velocity, the off-gas flow volume and/or the detected concentrations of one or more individual target off-gas components, the control system may then be used to outright control signals to control both input parameters in the furnace heating vessel, as well as past-combustion environmental controls, such as scrubbers operations and the like. In the case of BOF or EAF steelmaking furnaces, such controlled input parameters could include by way of non-limiting example vessel melt temperature, iron charging and/or scrap charging rates, carbon charging rates, and/or oxygen introduction, to control or optimize combustion parameters and steel production operation.

Accordingly, the present invention resides in various non-limiting aspects, and which include, without restriction as follows:

In a first aspect, an optical sensor assembly for sensing a velocity of at least part of an industrial combustion process off-gas flow, the sensor assembly comprising: a first beam emitter/optic sensor pair comprising a first energy beam emitter operable to emit a respective energy beam through a first portion of the off-gas flow, and a first optic sensor positioned for receiving and sensing the energy beam emitted from the first energy beam emitter, a second beam emitter/optic sensor pair comprising a second energy beam emitter operable to emit a respective energy beam through a second portion of the off-gas flow at a location spaced downstream from the first portion, and a second optic sensor positioned for receiving and sensing the energy beam emitted from the second energy beam emitter, wherein each respective energy beam comprises beam energy having an absorption profile corresponding to an absorption profile of at least one target species component of said off-gas flow, the first and second optic sensors operable to output electronic signals representative of the sensed energy beam to a processing assembly operable to correlate the electronic signals to absorption energy profile of the at least one target gas species of said off-gas stream, and wherein said processing assembly is selected to, correlate the electronic signals received from the first optic sensor to identify a gas absorption signature of said off-gas flow at a first position relative to at least part of the said first beam emitter/optic sensor pair, correlate the electronic signals received from said second optic sensor to identify the occurrence of the gas absorption signature at a second position relative to at least part of said second first beam emitter/optic sensor pair, and based at least in part on the time between the identification of the gas absorption signature at the first and second positions provide an output signal based on an identified velocity of at least part of the off-gas flow.

In another aspect, the present invention resides in an optical assembly for sensing a velocity of at least part of an industrial combustion process off-gas flow, the sensor assembly comprising: a first beam emitter/optic sensor pair comprising a first energy beam emitter operable to emit a respective energy beam through a first portion of the off-gas flow, and a first optic sensor positioned for receiving and sensing the energy beam emitted from the first energy beam emitter, a second beam emitter/optic sensor pair comprising a second energy beam emitter operable to emit a respective energy beam through a second portion of the off-gas flow at a location spaced downstream from the first portion, and a second optic sensor positioned for receiving and sensing the energy beam emitted from the second energy beam emitter, the first and second optic sensors operable to output electronic signals representative of the sensed energy beam to a processing assembly operable to correlate the electronic signals to an energy absorption signature of said off-gas stream, and wherein said processing assembly is selected to, correlate the electronic signals received from the first optic sensor to identify the energy absorption signatures of off-gas flow at a first position relative to at least part of the said first beam emitter/optic sensor pair, correlate the electronic signals received from said second optic sensor to identify the occurrence of the energy absorption signature at a second position relative to at least part of said second first beam emitter/optic sensor pair, and based at least in part on the time between the identification of the energy absorption signature at the first and second positions, provide an output signal based on an identified velocity of at least part of the off-gas flow.

In another aspect, the control system for an industrial furnace comprises a processor, and a sensor assembly electronically communicating with said processor for sensing a velocity of at least part of a furnace combustion process off-gas flow, the sensor assembly comprising: a first beam emitter/optic sensor pair comprising a first energy beam emitter operable to emit a respective energy beam through a first portion of the off-gas flow, and a first beam sensor positioned for receiving and sensing the energy beam emitted from the first energy beam emitter, a second beam emitter/energy beam sensor pair comprising a second energy beam emitter operable to emit a respective energy beam through a second portion of the off-gas flow at a location spaced downstream from the first portion, and a second beam sensor positioned for receiving and sensing the energy beam emitted from the second energy beam emitter, wherein each respective energy beam comprises beam energy having an absorption profile corresponding to an absorption profile of at least one target species component of said off-gas flow, the first and second beam sensors operable to output electronic signals representative of the sensed energy beam to a processor, the processor including programme instructions operable to: correlate the electronic signals received from the first beam sensor to an absorption energy profile of at least one, and preferably a plurality of target gas species of said off-gas stream and identify a gas absorption signature of said off-gas flow at a first position, correlate the electronic signals received from said second beam sensor to the absorption profile of the at least one, and preferably the plurality of the target gas species of the off-gas stream and identify the occurrence of the gas absorption signature at a second position spaced from the first position, and based at least in part on a time difference between the identification of the gas absorption signature at the first position and at the second position determine at least one of a flow velocity and/or a volume of at least part of the off-gas flow, and based on the determination, output of a control signal for at least one of a combustion process of the furnace and a downstream off-gas flow pollution control apparatus.

In yet another aspect, a furnace control system and/or method for the optimization of furnace combustion operations is provided, the system including: a combustion gas flow sensor assembly comprising, a first optic sensor disposed at a first position relative to a combustion gas flow, a second optic sensor disposed at a second position relative to said combustion gas flow, the second position being spaced a predetermined distance from said first position, each of the first and second optic sensors operable to receive the laser radiation from the incident laser, at least one photodetector optically coupled to at least one associated one of the first and second optic sensors, the at least one photodetector operable to generate electric signals in proportion to the laser energy received from the associated optic sensors, a data compiler communicating with the at least one photodetector for compiling energy at least one profile of laser energy sensed by each of first and second optic sensors based on the generated electric signals, a processing assembly for correlating at least a portion of the compiled energy profile of energy sensed by the second sensor and outputting a signal representative of at least one of the combustion gas velocity and the combustion gas volume based on a time difference between the correlated portions.

The assembly or system in accordance with any preceding or hereafter described aspects, wherein the combustion process off-gas flow comprises a furnace off-gas flow moving through a flue duct, the first beam emitter/optic sensor pair being positioned at a first upstream portion of the flue duct, the second beam emitter/optic sensor pair being positioned at a second portion of the flue duct spaced a distance downstream from the first upstream position.

The assembly or system in accordance with any preceding or hereafter described aspects, wherein the energy beam emitter and optic sensor of each of the first and second beam emitter/optic sensor pair are provided as part of a combined beam emitter/receptor head for positioning on a first side portion of the flue duct, and each of the first and second beam emitter/optic sensor pair further includes an associated reflector assembly, each reflector assembly being provided for positioning on a further side portion of the flue duct selected to receive and reflect the respective energy beam emitted towards the optic sensor of the associated beam emitter/optic sensor pair.

The assembly or system in accordance with any preceding or hereafter described aspects, wherein the optical sensor assembly comprises part of a furnace control system, wherein the output signal comprises a furnace control signal based on a determined velocity of the at least part of the off-gas flow.

The assembly or system in accordance with any preceding or hereafter described aspects, wherein the portion of the flue duct between the first beam emitter/optic sensor pair and the second beam emitter/optic sensor pair has predetermined geometry, the processing assembly operable to provide said output signal as an indicator of at least one of a velocity and a volume of said off-gas flow and/or a gas species thereof.

The assembly or system in accordance with any preceding or hereafter described aspects, wherein the processing assembly is operable to output a control signal to control at least one of a furnace combustion input and/or a downstream pollution control apparatus in response to the output signal.

The assembly or system in accordance with any preceding or hereafter described aspects, wherein the predetermined geometry comprises a substantially uniform geometry, and/or wherein the first beam emitter/optic sensor pair and the second beam emitter/optic sensor pair are mounted relative to said flue duct in substantially the identical orientation.

The assembly or system in accordance with any preceding or hereafter described aspects, wherein the first beam emitter/optic sensor pair is spaced a distance selected at between about 0.3 and about 5 meters, preferably 0.5 and 3 meters and most preferably about 0.7 and 1.5 meters from the second beam emitter/optic sensor pair.

The assembly or system in accordance with any preceding or hereafter described aspects, wherein each of the first and second beam emitters comprises a coherent light beam emitter operable to emit a coherent light beam, and preferably a tunable diode laser beam.

The assembly or system in accordance with any preceding or hereafter described aspects, wherein the sensor assembly further comprises a beam splitter and a tunable diode laser operable to output a laser beam to the beam splitter, the beam splitter being optically coupled to each of the first and second beam emitters for optically communicating substantially evenly split laser beam energy thereto for output as said coherent light beam.

The assembly or system in accordance with any preceding or hereafter described aspects, wherein said target species comprises one or more selected from the group consisting of $O_2$, $CH_4$, $H_2O$, $CO$ and $CO_2$.

The assembly or system in accordance with any preceding or hereafter described aspects, wherein said industrial combustion process is a steelmaking process, and more preferably a basic oxygen furnace or an electric arc furnace steelmaking process.

The assembly or system in accordance with any preceding or hereafter described aspects, wherein each energy beam comprises energy having an absorption profile corresponding to an absorption profile of at least one target species component of said gas flow, and said energy absorption signature comprises at least one selected from the group consisting of a total sensed energy beam, a sensed energy corresponding to the absorption profile of the at least one target species, and combinations thereof.

The assembly or system in accordance with any preceding or hereafter described aspects, wherein the industrial furnace further comprising: a flue duct for directing the off-gas flow, the energy beam emitter and beam sensor of each of the first and second beam emitter/energy beam sensor pair being provided as part of a combined beam emitter/receptor head for positioning along longitudinally spaced side portions of the flue duct, and wherein each of the first and second beam emitter/optic sensor pairs further includes an associated reflector assembly, each reflector assembly being provided for positioning along a side portion of the flue duct generally opposite to the associated beam emitter/receptor head and configured to receive and reflect the respective energy beam emitted through a generally central portion of said off-gas flow and towards the associated beam sensor.

The assembly or system in accordance with any preceding or hereafter described aspects, wherein the beam emitter/receptor head includes a tubular shroud having a hollow interior open to the flue duct, the beam emitter/receptor head configured to emit and receive beam energy along the interior of the shroud, and a purging gas source selectively operable to introduce a flow of purging gas flow along the interior of the shroud selected to dislodge dust or debris accumulated therein.

The assembly or system in accordance with any preceding or hereafter described aspects, wherein the portion of the flue duct between the first beam emitter/energy beam sensor pair and the second beam emitter/energy beam sensor pair has predetermined uniform geometry, and/or the processor operable to provide said control signal in response to the determined flow velocity and/or volume of said off-gas flow, or a one or more of said gas species thereof.

The assembly or system in accordance with any preceding or hereafter described aspects, wherein the flue duct is characterized by a substantially uniform geometry between the first beam emitter/energy beam sensor, and the second beam emitter/energy beam sensor, the first beam emitter/energy beam sensor pair and the second beam emitter/energy beam sensor pair being mounted to said flue duct in substantially the same relative orientation, and wherein the first beam emitter/energy beam sensor pair is spaced a distance selected at between about 0.3 and about 7 meters, and preferably about 0.5 and 3 meters downstream from the second beam emitter/energy sensor pair.

The assembly or system in accordance with any preceding or hereafter described aspects, wherein each of the first and second beam emitters comprises a coherent light beam emitter operable to emit a coherent light beam, and each of the first and second beam sensors comprise an optic sensor.

The assembly or system in accordance with any preceding or hereafter described aspects, wherein the sensor assembly further comprises a beam splitter and a tunable diode laser operable to output a laser beam to the beam splitter, the beam splitter being optically coupled to each of the first and second beam emitters for optically communicating split laser beam energy thereto for out therefrom as a said energy beam.

The assembly or system in accordance with any preceding or hereafter described aspects, wherein said target species comprises one or more selected from the group consisting of $O_2$, $CH_4$, $H_2O$, $CO$, and $CO_2$.

The assembly or system in accordance with any preceding or hereafter described aspects, wherein said industrial furnace comprises a steelmaking furnace selected from the group consisting of a basic oxygen furnace and an electric arc furnace.

The use of assembly or system in accordance with any preceding or hereafter described aspects, characterized in that said combustion process off-gas flow comprises an off-gas flow from a steelmaking furnace, and the target species components of the off-gas stream include CO and $CO_2$, the steelmaking furnace comprising a heating vessel for heating an iron source and a carbonaceous material, and a lance for the selective introduction of oxygen into the heating vessel, wherein said output signal comprises a furnace control signal comprises a lance control signal selected to limit lance operation based at least in part on a detected volume of CO and/or $CO_2$ in said off-gas flow.

The use of assembly or system in accordance with any preceding or hereafter described aspects, wherein the processing assembly is further operable to receive data representation of an input amount of said carbonaceous material in said heating vessel, and wherein lance control signal is based at least in part on said data.

The use of assembly or system in accordance with any preceding or hereafter described aspects, wherein said data is received during a steelmaking heat in substantially real time.

The use of assembly or system in accordance with any preceding or hereafter described aspects, wherein said lance control signal is selected to control at least one of slag oxidation and melt decarburization in said steelmaking furnace.

The assembly or system in accordance with any preceding or hereafter described aspects, wherein said steelmaking furnace comprises basic oxygen furnace and said combustion process off-gas flow comprises a basic oxygen furnace off-gas flow.

The use of assembly or system in accordance with any preceding or hereafter described aspects, wherein said steelmaking furnace comprise an electric arc furnace and said combustion off-gas flow comprises an electric arc furnace off-gas flow The furnace control system and/or method or use according to the preceding or hereafter described aspects comprising of tunable diode laser source which is used for projecting a first portion of an optical beam generated by a laser source through a volume of gases evolved from the melt chamber, the volume of gases including at least one indicator gas; detecting the first portion of the optical beam after the first portion has passed through the volume of gases; projecting a second portion of the optical beam through a reference volume of gases, the reference volume of gases comprising the at least one indicator gas; detecting the second portion of the optical beam after the second portion has passed through the reference volume of gases; based on the detected first and second portions of the optical beam, controllably changing an output frequency of the laser source to substantially correspond with an absorption line of the at least one indicator gas; determining a real-time concentration of the at least one indicator gas based on the detected first and second portions of the optical beam;

The furnace control system and/or method of using the system according to any of the preceding or hereafter described aspects, wherein the first portion of the optical beam is detected by an optical detector.

The furnace control system and/or method of any of the preceding or hereafter described aspects, wherein the first portion of the optical beam is focused on receiving optics, and wherein the optical detector is remotely positioned and operably connected to the receiving optics via an optical connector.

The furnace control system and/or method of any of the preceding or hereafter described aspects, further comprising reflecting the first portion of the optical beam across the volume of gases one or more times.

The furnace control system and/or method of any of the preceding or hereafter described aspects, further comprising detecting a change in the real-time concentration corresponding to a predetermined profile indicative of a process control.

The furnace control system and/or method of any of the preceding or hereafter described aspects, further comprising detecting a real time off-gas temperature by use of a selected wavelength line.

The furnace control system and/or method of any of the preceding or hereafter described aspects, further comprising a plurality of said collimators for laser emission, for two points of detection at the desired location.

The furnace control system and/or method of any of the preceding or hereafter described aspects, wherein the furnace comprises a steelmaking furnace, and the first and second optic sensors are positioned in or immediately adjacent to said combustion gas flow along a flue gas discharge pipe.

The furnace control system and/or method of any of the preceding or hereafter described aspects, wherein said emission energy received by the first and second optic sensors comprise resultant optical beam after the volume absorption of the gases present by an adjacent portion of said combustion gas flow.

The furnace control system and/or method of any of the preceding or hereafter described aspects, wherein said laser radiation received by the first and second optic sensors comprises light energy of substantially an entire width of a portion of the combustion gas flow moving past the first and second positions, respectively.

The furnace control system and/or method of any of the preceding or hereafter described aspects, wherein the sensed radiation energy is radiation energy emitted from absorption of at least one of an $O_2$, CO and/or a $CO_2$ component of the combustion gas flow from the incident laser beam.

The furnace control system and/or method of any of the preceding or hereafter described aspects, wherein the steelmaking furnace is selected from an EAF and a BOF, at least one of the first and second optic probes including a directional purging system and/or a cooling system.

The furnace control system and/or method of any of the preceding or hereafter described aspects operable to provide real time models to calculate decarburization and slag oxidation.

The furnace control system and/or method of any of the preceding or hereafter described aspects operable to provide real time (qualitative) and the value (quantitative) of the decarburization can be used for the improved control of the EAF lance oxygen.

The furnace control system and method of any of the preceding aspects, wherein the gas flue duct pipe has a generally predetermined fixed geometry between the first and second positions, and wherein the processing assembly operates to determine off-gas species component and/or furnace combustion gas volume by comparing the velocity combustion gas flow as a ratio of the time of flight of the combustion gas between the first and second optic probes with the predetermined geometry.

BRIEF DESCRIPTION OF THE DRAWINGS

Reference may now be had to the following detailed description, taken together with the accompanying in which.

DETAILED DESCRIPTION OF THE PREFERRED EMBODIMENTS

Figure 1:
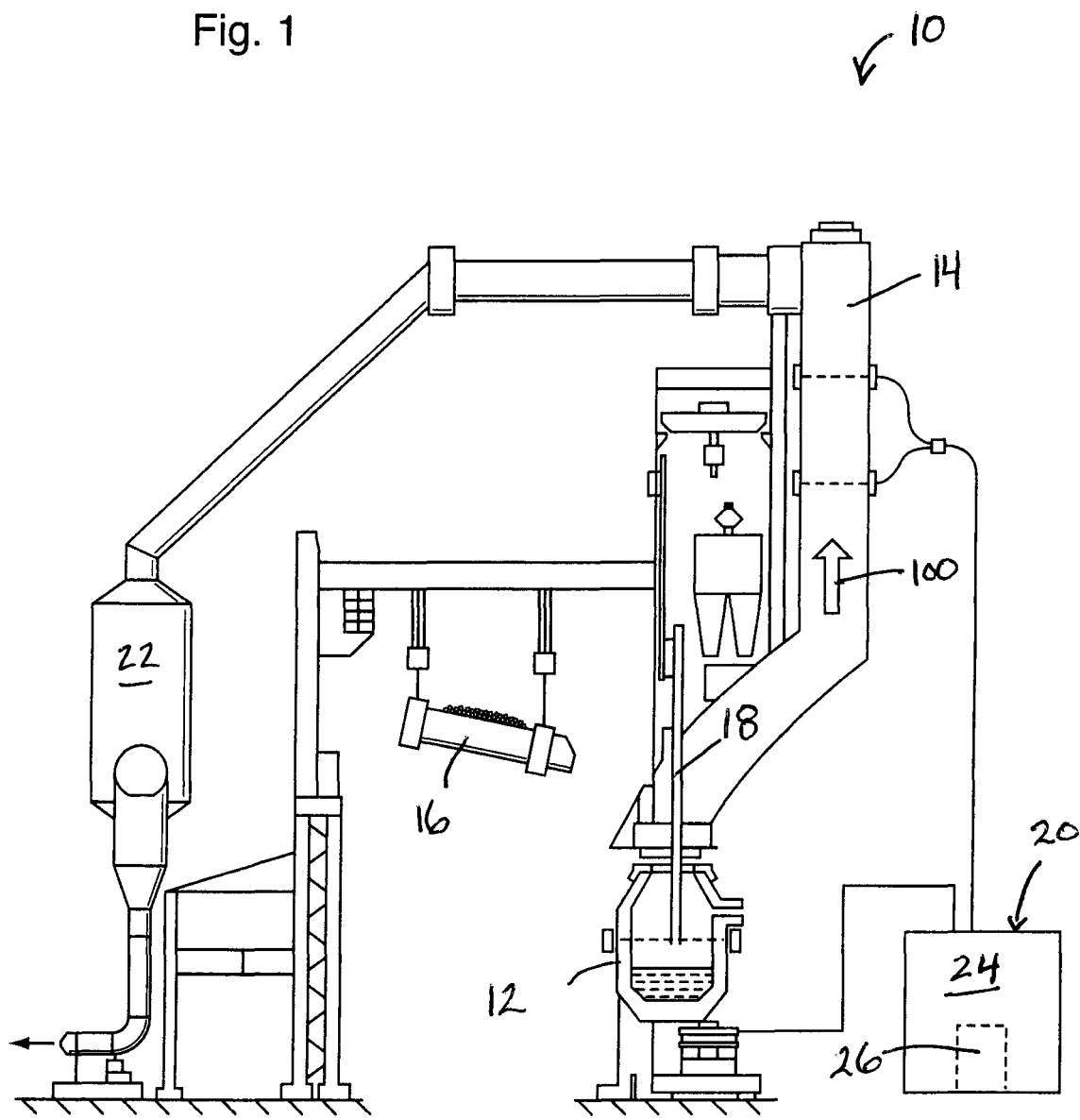
FIG. 1 shows schematically a basic oxygen furnace (BOF) installation in accordance with a preferred aspect of the invention.
Figure 2:
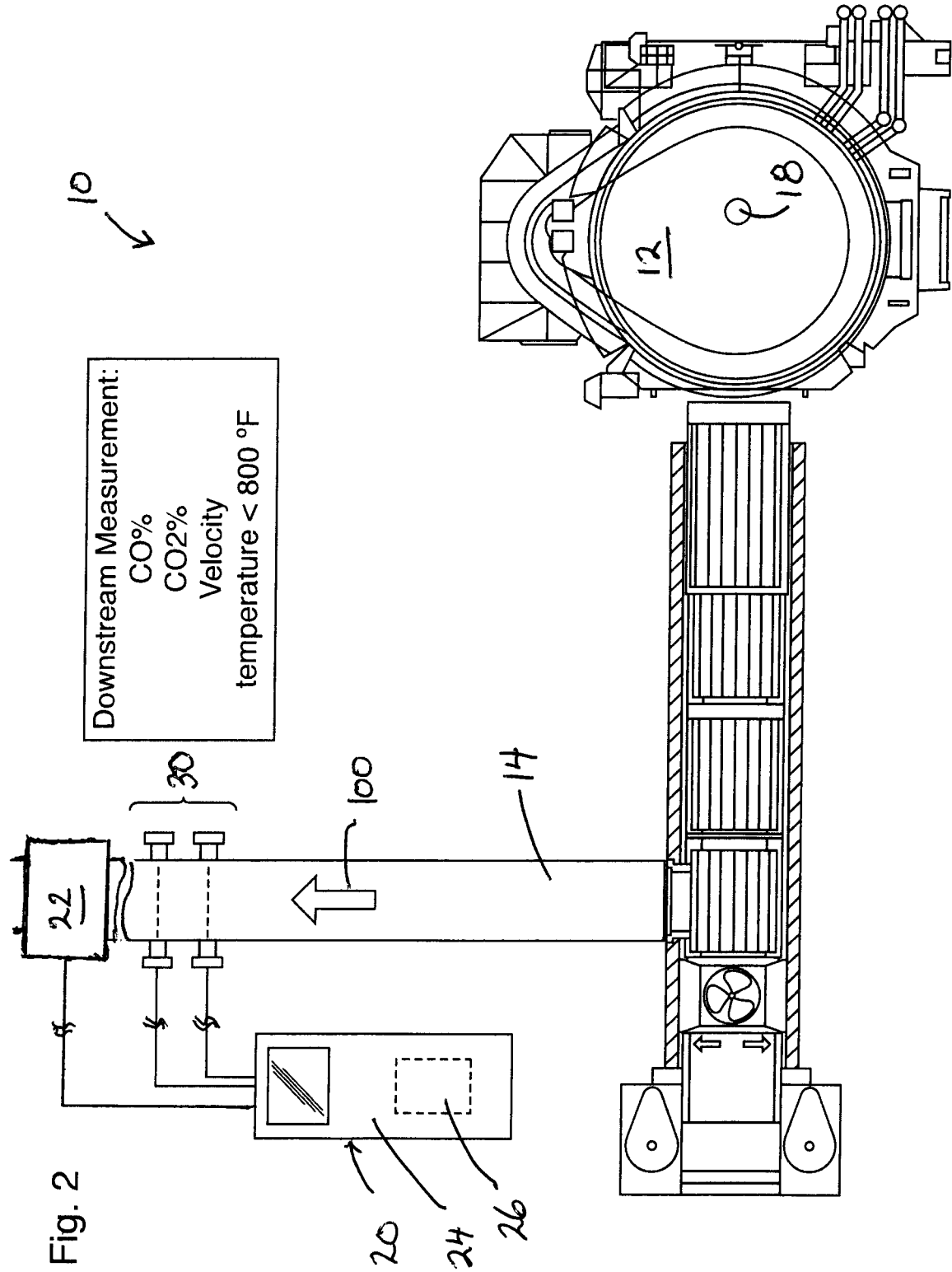
FIG. 2 shows schematically a furnace control system which incorporates an off-gas flow velocity sensor assembly used in the BOF furnace installation of FIG. 1.

Reference may be had to FIGS. 1 and 2 which illustrate a basic oxygen furnace (BOF) installation 10 used in steelmaking, in accordance with a preferred embodiment. As will be described, installation 10 includes a heating vessel 12, an off-gas flue duct 14, a steel and carbon charging box 16, an oxygen lance 18, a furnace control system 20 and an off-gas scrubber assembly 22.

During a heat in steelmaking operations, the heating vessel 12 receives as an input from the charging box 16, scrap iron and carbonaceous material, which is heated and melted in a steel manufacturing heat. Concurrently, oxygen is input from the lance 18 over the heated material to ignite and lower the carbon content of molten iron. During the heat process, the ignition of the carbon and iron reduction results in a furnace off-gas stream or flow 100 along and outwardly from the flue duct 14, via the off-gas scrubber assembly 22. Depending on the specific furnace input material, the resulting off-gas flow 100 is typically composed of a number of gas species, and which typically include CO, $CO_2$, $O_2$, $CH_4$, $H_2O$, as well as others.

The heating vessel 12 is open at its upper end to the off-gas flue duct 14 for receiving and directing the combustion off-gas flow 100 generated by the vessel 12 operation to the scrubber assembly 22, for $CO_2$ capture, particulate and/or contamination removed prior to exhausting to the atmosphere.

The furnace control system 20 is provided for the overall control of the installation 10, including the input of scrap, iron and/or carbon charging into the vessel, vessel 12 heating temperatures, oxygen charging into the vessel 12 by way of the oxygen lance 18, as well as scrubber assembly 22 operation. The furnace control system 20 includes a processor 24 and an off-gas sensor assembly 30 which, as will be described, operates to signal to the processor 24 the subsequent generation of system control signals to regulate one or more operating parameters of the heating vessel 12 and/or the input therein, and/or the operation of the scrubber assembly 22, depending on sensed real-time velocity and/or volumes of the off-gas flow 100, and/or the concentrations and/or volumes of one or more of individual off-gas species.

In a preferred embodiment, the processor 24 includes memory 26 which has stored therein one or more predetermined and/or computer modeled combustion off-gas velocity, volume and/or species content profiles. The stored profiles may represent one or more target or optimized furnace heats; or may relate to an optimized or target scrubber assembly operations.

Figure 3:
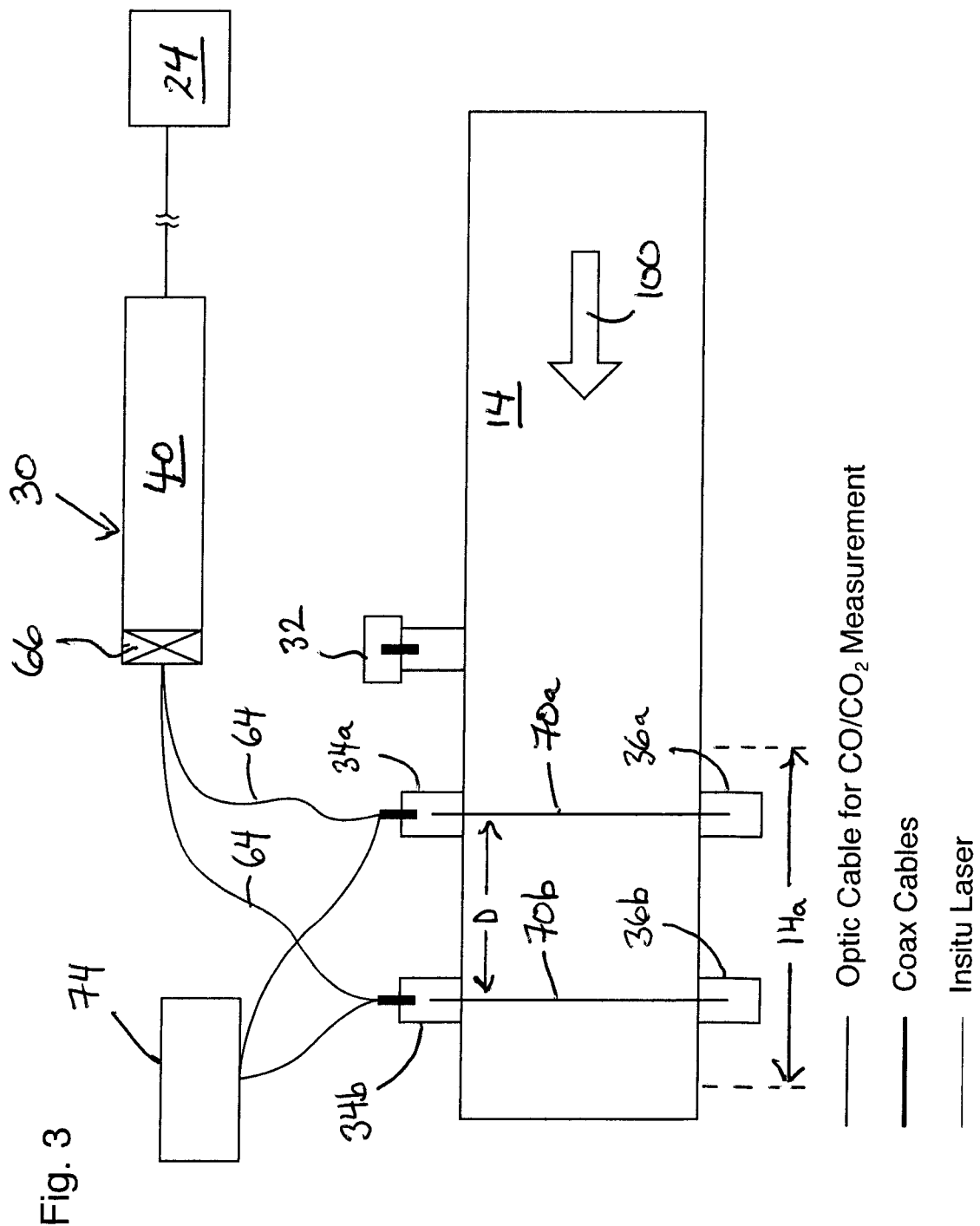
FIG. 3 shows schematically the positioning of associated coherent light emitter/optical sensor pairs and optic reflectors used in the optical off-gas flow velocity sensor assembly shown in FIG. 2.

FIG. 3 shows best, the off-gas velocity sensor assembly 30 as being electronically coupled to the processor 24. As will be described the sensor assembly 30 is preferably adapted to provide the real-time measurement of the velocity combustion off-gas flow 100, and/or the off-gas flow 100 volume or individual species volumes moving through the flue duct 14 during vessel 12 heat operation. Data representing sensed off-gas flow 100 velocity and/or volume is used either directly, or in combination with temperature and/or concentration measurements of one or more off-gas species components, such as CO % vol., $CO_2$% vol., $CH_4$% vol., to then effect the control of one or more of the vessel 12 input parameters, and/or the scrubber assembly 22, with a view to optimizing the operation of the BOF installation 10. Preferably, a separate temperature sensor 32 (shown in FIG. 3) is provided along flue duct in proximity to the off-gas velocity sensor assembly 30. The temperature sensor 30 may be in a form of a thermocouple and is used to detect the temperature of the off-gas flow 100 as it moves along the duct 14, past the velocity sensor assembly 30. Alternatively, off-gas flow 100 temperature may be detected optically.

FIG. 3 shows best the off-gas sensor assembly 30 as including two associated pairs of laser emitters/optic sensors 34a, 34b, an optic reflector 36a, 36b, respectively associated with each emitter/optic sensor pair 34a, 34b, and a tunable diode laser 40 which is provided as a coherent light source. The pairs of laser emitter/optic sensors 34a, 34b and optic reflectors 36a, 36b are preferably positioned along a portion of the flue duct 14a which is selected having a substantially uniform, predetermined cross-section geometry, and with a preselected spacing from each other. Most preferably, the portion of the flue duct 14a is provided having a constant cylindrical or rectangular cross-sectional profile, without bends or internal obstructions. Each laser emitter/optical sensor pair 34a, 34b is mounted centrally to a side of the flue duct 14, with the associated optic reflector 36a, 36b disposed generally opposed thereto on the opposite side of the flue duct 14. The laser emitter/optic sensor 34b and its associated optic reflector 36b are spaced a known distance longitudinally downstream in the flow direction of the combustion off-gas flow 100 from the laser emitter/optic sensor pair 34a, and optic reflector 36a.

Figure 4:
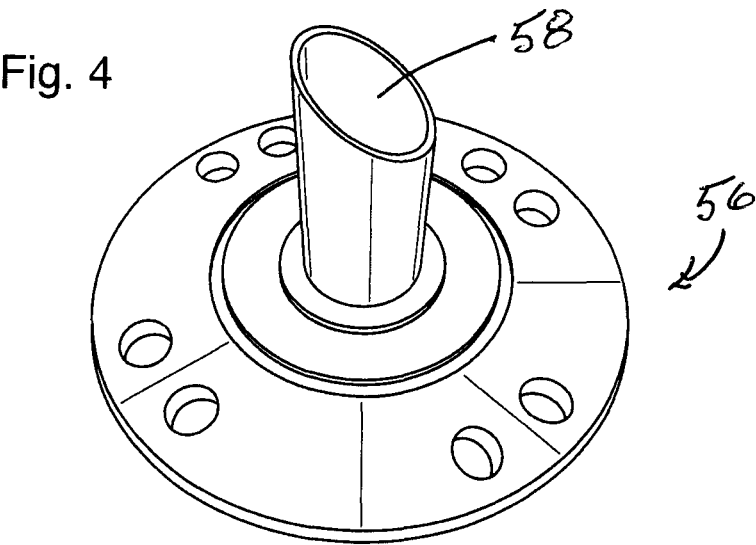
FIG. 4 shows a perspective view of a housing shroud for use with coherent light emitter/optic sensor pairs illustrated in FIG. 3.
Figure 5:
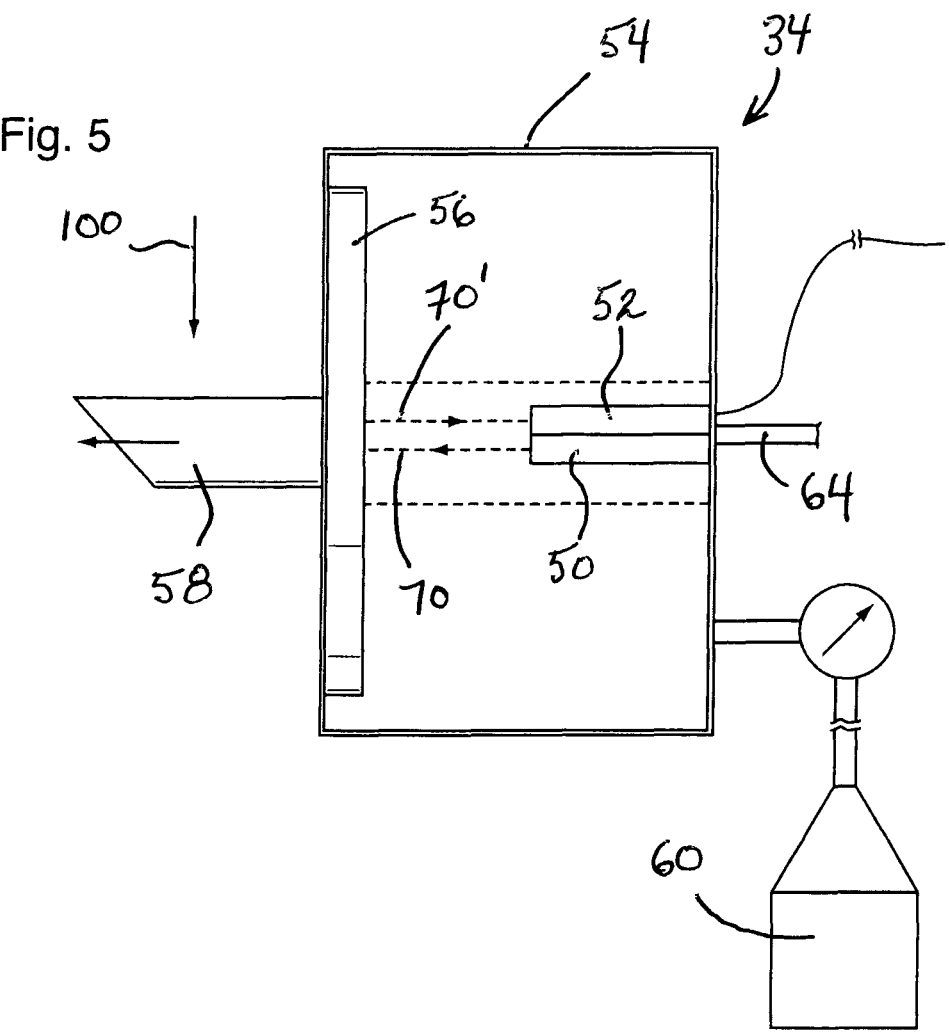
FIG. 5 illustrate schematically the positioning of a coherent light emitter/optic sensor used in the off-gas flow velocity sensor assembly, in accordance with a preferred embodiment of the invention.

As shown best in FIGS. 4 and 5, each laser emitter/optic sensor pair 34 includes an optic emitter lens 50 and an optic receiver 52 which preferably are mounted as part of a modular preassembly within an enclosure housing 54. The enclosure housing 54 is open to the interior of the flue duct 14 by way of a shroud 56. As shown best in FIG. 4, the shroud 56 is provided with a tubular extension 58 which has an axial length selected to project inwardly from the side of the duct 14, part way within the off-gas flow 100, and which is open to the associated optic reflector 36a, 36b.

Optionally, a pressurized gas source 60 may be provided in fluid communication with an interior of the enclosure housing 54. The pressurized gas source 60 is selectively operable to introduce a pressurized gas flow into the housing 54 and outwardly from the shroud extension 58, to dislodge any dust or debris which may have accumulated therein.

Each optic emitter lens 50 optically communicates with the laser 40 by a suitable optic cable 64. Although not essential, most preferably, the laser 40 is provided with an optic splitter or multiplexer 66. The optical splitter/multiplexer 66 is in turn optically coupled with the lens 50 of each laser emitter/optical sensor pair 34a, 34b via the fiber optic cabling 64. In use, the velocity sensor assembly 30 thus output across a portion of the off-gas flow 100, separate incident laser beams 70a, 70b having equal wavelength.

The coherent light beam generated in the laser 40, is optically split by the multiplexer 66 into separate energy beams, for output from the emitter lens 50 of each laser emitter/optic sensor pair 34a, 34b as a respective emitted laser beam 70a, 70b. Each optic emitter lens 50 is thus adapted to emit across the flue duct 14 and through a central portion of the combustion off-gas flow 100, towards the associated optic reflector 36a, 36b, a respective output incident laser beam 70a, 70b.

In a simplified arrangement, the optic reflectors 36 are each provided as an optical mirror or retroreflector. The laser energy impacting the optic reflectors 36a, 36b is reflected back across the combustion off-gas flow 100, into the enclosure housing 54 as a return reflected beam (shown schematically in FIG. 5 as 70') where it is received by the associated optic receiver 52. Each optic reflector 36a, 36b is preferably positioned to receive and reflect the portion of the incident laser beam 70a, 70b back through the central portion of off-gas flow 100, with the longitudinal spacing of the laser emitter/optic sensor pair 34a, 34b resulting in the laser beams 70a, 70b being propagated across the flue duct 14 at a known spacing D from each other.

Preferably, the laser emitter/optic sensor pairs 34a, 34b and their associated optic reflector 36a, 36b are provided in the identical orientation and position relative to the flue duct 14. In this configuration, each associated incident laser beam 70a, 70b and the reflected beam energy emitted and reflected, pass substantially parallel to each other and through substantially the same portion of the combustion off-gas flow 100 moving along the flue duct 14.

While the preferred construction describes a tunable diode, the laser 40 is operated to generate the output a coherent light beam which is split into two equal energy components or multiplexed by the optical splitter/multiplexer 66, the invention is not limited. Other types of energy sources, and/or the use of separate lasers as individual coherent light sources may also be used.

The reflectors 36a, 36b are positioned to reflect the beam energy received thereon, as reflected laser beam energy 70' back to the optic receiver 52 of the respective associated emitter/optic sensor pair 34a, 34b. The optic receivers 52 are in turn electronically coupled to a photodetector 74, whereby the energy of the respective reflected portion of the photon beams 70a, 70b received and detected by the optic receptor 52 and converted to electrical signals, which in turn are communicated to the processor 24. The processor 24 compares the electric signals transmitted from the photodetector 74, and which is representative of the detected energy from each reflected photon beam 70a, 70b at each laser emitter/optic sensor pair 34a, 34b, to identify the absorption signature, and more preferably concentrations of one or more target gas species in the off-gas flow 100. Most preferably, the processor 24 is used to identify the overall absorption profile of the off-gas flow and/or the absorption profile for one or more of $O_2$, $CH_4$, CO and/or $CO_2$ species components within the combustion off-gas flow 100 and temperature of the off-gas flow at individual points in time.

The processor memory 26 preferably also has stored therein data which represents both the geometry of the portion 14a of gas flue duct 14, as well as data representing the longitudinal distance D between each emitted laser beams 70a, 70b relative to each other in the longitudinal direction of the gas flue duct 14.

The processor 24 operates to identify portions of the combustion off-gas flow 100 having a specific temperatures, and the overall gas flow absorption profile and/or $O_2$, $CH_4$, CO and/or $CO_2$ species concentrations by their respective absorption profile in the off-gas flow 100, and generate at the upstream laser emitter/optic sensor pair 34a, a gas absorption signature for the off-gas flow as it moves along the flue duct 14. The processor 24 further operates using data received from the downstream laser emitter/optic sensor pair 34b to identify the portions of the off-gas flow having substantially the same absorption signature. Based on the delay in detecting the absorption signature at the second laser emitter/optic sensor pair 34b, the processor 24 may thus determine the velocity of the off-gas flow 100 or the movement of one or more target species therein, along the flue 14. By determining the time of flight of the absorption signature, and preferably concentrations of selected $O_2$, $CH_4$, CO and/or $CO_2$ components between each laser emitter/optic sensor pair 34a, 34b, the processor 24 may operate to calculate both the true velocity of the combustion off-gas flow 100 across the entire duct 14 as it moves through the off-gas flue duct 14; and based on the known geometry of the portion of the flue duct 14a, the overall combustion off-gas stream or individual species volumes.

The detected gas flow velocity and/or volumes may also be compared with the target values and/or optimized profiles stored in memory 26. The system processor 24 is then used to output in real time, control signals to adjust furnace inputs, including for example one or more of oxygen concentration, input feed materials, melt temperatures or the like within the heating vessel 12 during heat operation; as well as s operation parameters of the scrubber assembly 22.

FIG. 5 illustrates a preferred construction for a laser emitter/optic sensor pair 34 preassembly in accordance with a preferred embodiment of the invention. Most preferably, each laser emitter/optic sensor pair 34 is preassembled for the in situ transmission and reception of the incident and reflected laser beams 70 across the off-gas flue duct 14 during heating vessel 12 operation. The use of in situ laser beam energy advantageously allows for faster and reliable measurement of $O_2$ percentage, CO percentage, $CO_2$ percentage (or their ppm), in additional to the off-gas velocity. The applicant has appreciated that the use of in situ lasers for optically determining off-gas velocity advantageously eliminates or minimizes the need for re-calibration.

The applicant has appreciated that the construction of the laser emitter/optic sensor pair 34 shown in FIGS. 4 and 5 also advantageously avoids the requirement to position any electronics within the duct 14, whilst allowing the laser 40 to be located remotely, away from dust and/or high temperature environments.

It is also recognized that measurement of $O_2\%$, $CH_4\%$, CO %, and/or $CO_2\%$, concentrations, off-gas velocity and the temperature of the combustion gas in the combustion off-gas flow 100 may enable the calculation of the amount of gaseous carbon (lbs or lbs/s) leaving the EAF system. It is recognized that qualitative feature and the quantitative value of the decarburization in turn may be used for the improved control of the EAF lance 18, and $O_2$ injection control.

Furthermore, real time models may also calculate decarburization and/or slag oxidation, as follows:

Carbon IN (Scrap+Cinj+Methane)=Carbon OUT+ Bath Carbon

Carbon OUT=(CO %+$CO_2$%)*OG Flow downstream

Decarburization=dC/dt=CarbonOUT/seconds    Decarburization:

Carbon out calculation may depend on the off-gas system information being available. In particular, it is expected that if the oxidation is efficient and carbon is available in the bath that Carbon will evolve from the bath and be measured by the downstream off-gas system.

With more efficient oxidation it would be expected that using the oxygen lance 18, $O_2$ and carbon in the off-gas flow 100 will increase, and bath carbon will decrease, provided that carbon inlet remains constant. Therefore using the Carbon OUT calculation (Decarburization lb/sec) it may be possible to evaluate if and when a lance 18 should be turned on or off.

If the oxidation is not efficient, it would be possible for high carbon to remain in the bath while carbon out remains constant or decreases, even if oxygen is injected. The injected oxygen will result in an increased FeO. This particular situation cannot be detected measuring Carbon OUT only. It can, however, be discovered if the Carbon IN is measured.

Therefore the furnace control system 20 may allow for the optimization of the oxygen lance 18 $O_2$ system, to make sure it is operating at the highest efficiency.

Oxidation of Slag

It is proposed that slag oxidation may be modeled as follows:

Slag Oxidation generated=Total $O_2$ (Including Air)– $O_2$ for Carbon out

This assumes that only lance $O_2$ can decarburize=>it generates CO, and air entering the furnace and the tunnel post combust the CO.

As a result, slag Oxidation generated=Lance O2–O2 for CO from bath.

Where moles of CO from bath=moles of Carbon OUT–moles of C inj–moles of $CH_4$.

Without being bound by a particular theory, the calculation of "slag oxidation generated" may provide direct information of the amount of oxygen in the slag ($SiO_2$, MnO, FeO). Assuming that the amount of Si and Mn in the slag do not vary significantly from heat to heat, the "slag oxidation generated" will be dependent on the FeO generated (lb). A basic correlation between FeO % and bath $O_2$ ppm exists, and therefore it may be possible to evaluate the bath ppm based on the calculated "Slag oxidation generated".

If oxidation is efficient, the correlation between Slag FeO and bath $O_2$ ppm (similarly C in the bath) is expected to remain. If the oxidation is not efficient it is possible that FeO in the slag increases while Carbon in the bath remains high. This situation is what generally leads to "carbon boil" reactions.

Therefore based on the foregoing, the furnace control system 20 may also be useful for the optimization of the lance 18 and the introduction of $O_2$ into system to make sure it is operating at the highest efficiency. Possible lance 18 $O_2$ control may thus be adjusted based on one or more of decarburization curve; effect on decarburization curve; and/or Slag Oxidation.

End Point control may also be adjusted based on Slag Oxidation; and/or off-gas features.

Although the detailed description describes the preferred embodiment as including two associated laser emitter and optical sensor pairs 34a, 34a, the invention is not so limited. It is to be appreciated that additional pairs of associated laser emitter/optical sensors pairs may also 34 may be provided for increased redundancies and/or accuracies.

Although the preferred embodiment describes the use of a tunable diode laser 40 as coherent light source, and the use of the furnace control system 20 as part of a BOF installation 10, the invention is not so limited. It is to be appreciated that different energy on coherent light sources could also be used. In addition, the control system 20 of the present invention is equally suited for a number of different combustion and industrial furnace applications. Such applications may include, without restriction, other steelmaking furnaces such as EAF furnaces, as well as cement kilns, incinerator applications and the like.

We claim:

1. An optical sensor assembly for sensing a velocity of at least part of an industrial combustion process off-gas flow, the sensor assembly comprising:

a first beam emitter/optic sensor pair comprising a first energy beam emitter operable to emit a respective energy beam through a first portion of the off-gas flow, and a first optic sensor positioned for receiving and sensing the energy beam emitted from the first energy beam emitter, a second beam emitter/optic sensor pair comprising a second energy beam emitter operable to emit a respective energy beam through a second portion of the off-gas flow at a location spaced downstream from the first portion, and a second optic sensor positioned for receiving and sensing the energy beam emitted from the second energy beam emitter, wherein each respective energy beam comprises beam energy having an absorption profile corresponding to an absorption profile of at least one target species component of said off-gas flow, the first and second optic sensors operable to output electronic signals representative of the sensed energy beam to a processing assembly operable to correlate the electronic signals to absorption energy profile of the at least one target gas species of said off-gas stream, and wherein said processing assembly is selected to, correlate the electronic signals received from the first optic sensor to identify a gas absorption signature of said off-gas flow at a first position relative to at least part of the said first beam emitter/optic sensor pair, correlate the electronic signals received from said second optic sensor to identify the occurrence of the gas absorption signature at a second position relative to at least part of said second beam emitter/optic sensor pair, and based at least in part on the time between the identification of the gas absorption signature at the first and second positions, provide an output signal based on an identified velocity of at least part of the off-gas flow.

2. The sensor assembly as claimed in claim 1, wherein the combustion process off-gas flow comprises a furnace off-gas flow moving through a flue duct, the first beam emitter/optic sensor pair being positioned at a first upstream portion of the flue duct, the second beam emitter/optic sensor pair being positioned at a second portion of the flue duct spaced a distance downstream from the first upstream position.

3. The sensor assembly as claimed in claim 2, wherein the energy beam emitter and optic sensor of each of the first and second beam emitter/optic sensor pair are provided as part of a combined beam emitter/receptor head for positioning on a first side portion of the flue duct, and each of the first and second beam emitter/optic sensor pair further includes an associated reflector assembly, each reflector assembly being provided for positioning on a further side portion of the flue duct selected to receive and reflect the respective energy beam emitted towards the optic sensor of the associated beam emitter/optic sensor pair.

4. The sensor assembly as claimed in claim 2, wherein the optical sensor assembly comprises part of a furnace control system, wherein the output signal comprises a furnace control signal based on a determined velocity of the at least part of the off-gas flow.

5. The sensor assembly as claimed in claim 2, wherein the portion of the flue duct between the first beam emitter/optic sensor pair and the second beam emitter/optic sensor pair has predetermined geometry, the processing assembly operable to provide said output signal as an indicator of at least one of a velocity and a volume of said off-gas flow and/or a gas species thereof.

6. The sensor assembly as claimed in claim 5, wherein the processing assembly is operable to output a control signal to control at least one of a furnace combustion input and/or a downstream pollution control apparatus in response to the output signal.

7. The sensor assembly as claimed in claim 5, wherein the predetermined geometry comprises a uniform geometry, and/or wherein the first beam emitter/optic sensor pair and the second beam emitter/optic sensor pair are mounted relative to said flue duct in the identical orientation.

8. The sensor assembly as claimed in claim 2, wherein said target species comprises one or more selected from the group consisting of $O_2$, $CH_4$, $H_2O$, CO and $CO_2$.

9. The sensor assembly as claimed in claim 8, wherein said industrial combustion process is a basic oxygen furnace or an electric arc furnace steelmaking process.

10. Use of the sensor assembly as claimed in claim 2, characterized in that said combustion process off-gas flow comprises an off-gas flow from a steelmaking furnace, and the target species components of the off-gas stream include CO and CO2,
   the steelmaking furnace comprising a heating vessel for heating an iron source and a carbonaceous material, and a lance for the selective introduction of oxygen into the heating vessel,
   wherein said output signal comprises a furnace control signal that comprises a lance control signal selected to limit lance operation based at least in part on a detected volume of CO and/or CO2 in said off-gas flow.

11. The use according to claim 10, wherein the processing assembly is further operable to receive data representation of an input amount of said carbonaceous material in said heating vessel, and wherein the lance control signal is based at least in part on said data.

12. The use according to claim 11, wherein said data is received during a steelmaking heat in real time.

13. The use according to claim 12, wherein said lance control signal is selected to control at least one of slag oxidation and melt decarburization in said steelmaking furnace.

14. The use according to claim 12, wherein said steelmaking furnace comprises basic oxygen furnace and said combustion process off-gas flow comprises a basic oxygen furnace off-gas flow.

15. The use as claimed in claim 12, wherein said steelmaking furnace comprise an electric arc furnace and said combustion off-gas flow comprises an electric arc furnace off-gas flow.

16. The sensor assembly as claimed in claim 1, wherein the first beam emitter/optic sensor pair is spaced a distance selected between 0.3 meters and 5 meters from the second beam emitter/optic sensor pair.

17. The sensor assembly as claimed in claim 1, wherein each of the first and second beam emitters comprises a coherent light beam emitter operable to emit a coherent light beam.

18. The sensor assembly as claimed in claim 1, wherein the sensor assembly further comprises a beam splitter and a tunable diode laser operable to output a laser beam to the beam splitter, the beam splitter being optically coupled to each of the first and second beam emitters for optically communicating evenly split laser beam energy thereto for output as said coherent light beam.

19. A control system for an industrial furnace comprising a processor, and a sensor assembly electronically communicating with said processor for sensing a velocity of at least part of a furnace combustion process off-gas flow, the sensor assembly comprising:
   a first beam emitter/energy beam sensor pair comprising a first energy beam emitter operable to emit a respective energy beam through a first portion of the off-gas flow, and a first beam sensor positioned for receiving and sensing the energy beam emitted from the first energy beam emitter,
   a second beam emitter/energy beam sensor pair comprising a second energy beam emitter operable to emit a respective energy beam through a second portion of the off-gas flow at a location spaced downstream from the first portion, and a second beam sensor positioned for receiving and sensing the energy beam emitted from the second energy beam emitter,
   wherein each respective energy beam comprises beam energy having an absorption profile corresponding to an absorption profile of at least one target species component of said off-gas flow,
   the first and second beam sensors operable to output electronic signals representative of the sensed energy beam to the processor, the processor including program instructions operable to:
   correlate the electronic signals received from the first beam sensor to an absorption energy profile of at least one target gas species of said off-gas stream and identify a gas absorption signature of said off-gas flow at a first position,
   correlate the electronic signals received from said second beam sensor to the absorption profile of the at least one target gas species of the off-gas stream and identify the occurrence of the gas absorption signature at a second position spaced from the first position, and
   based at least in part on a time difference between the identification of the gas absorption signature at the first position and at the second position determine at least one of a flow velocity and/or a volume of at least part of the off-gas flow, and based on the determination, output of a control signal for at least one of a combustion process of the furnace and a downstream off-gas flow pollution control apparatus.

20. The control system as claimed in claim 19, wherein the industrial furnace further comprising:
   a flue duct for directing the off-gas flow,
   the energy beam emitter and beam sensor of each of the first and second beam emitter/energy beam sensor pair being provided as part of a combined beam emitter/receptor head for positioning along longitudinally spaced side portions of the flue duct, and wherein each of the first and second beam emitter/energy beam sensor pairs further includes an associated reflector assembly,
   each reflector assembly being provided for positioning along a side portion of the flue duct generally opposite to the associated beam emitter/receptor head and configured to receive and reflect the respective energy beam emitted through a generally central portion of said off-gas flow and towards the associated beam sensor.

21. The control system as claimed in claim 20, wherein the beam emitter/receptor head includes a tubular shroud having a hollow interior open to the flue duct, the beam emitter/receptor head configured to emit and receive beam energy along the interior of the shroud, and
   a purging gas source selectively operable to introduce a flow of purging gas flow along the interior of the shroud selected to dislodge dust or debris accumulated therein.

22. The control system as claimed in claim 20, wherein the flue duct is characterized by a uniform geometry between the first beam emitter/energy beam sensor pair, and the second beam emitter/energy beam sensor pair, the first beam emitter/energy beam sensor pair and the second beam emitter/energy beam sensor pair being mounted to said flue duct in the same relative orientation, and wherein the first beam emitter/energy beam sensor pair is spaced a distance selected between 0.3 meters and 7 meters downstream from the second beam emitter/energy beam sensor pair.

23. The control system as claimed in claim 22, wherein each of the first and second beam emitters comprises a coherent light beam emitter operable to emit a coherent light beam, and each of the first and second energy beam sensors comprise an optic sensor.

24. The control system as claimed in claim 19, wherein the portion of the flue duct between the first beam emitter/energy beam sensor pair and the second beam emitter/energy beam sensor pair has predetermined uniform geometry, the processor operable to provide said control signal in response to the determined flow velocity and/or volume of said off-gas flow, or a one or more of said gas species thereof.

25. The control system as claimed in claim 19, wherein the sensor assembly further comprises a beam splitter and a tunable diode laser operable to output a laser beam to the beam splitter, the beam splitter being optically coupled to each of the first and second beam emitters for optically communicating split laser beam energy therefrom as a said energy beam.

26. The control system as claimed in claim 19, wherein said target species comprises one or more selected from the group consisting of $O_2$, $CH_4$, $H_2O$, $CO$, and $CO_2$, and wherein said gas absorption signature includes at least one target species signature.

27. The control system as claimed in claim 26, wherein said industrial furnace comprises a steelmaking furnace selected from the group consisting of a basic oxygen furnace and an electric arc furnace.

28. An optical sensor assembly for sensing a velocity of at least part of an industrial combustion process off-gas flow, the sensor assembly comprising:

a first beam emitter/optic sensor pair comprising a first energy beam emitter operable to emit a respective energy beam through a first portion of the off-gas flow, and a first optic sensor positioned for receiving and sensing the energy beam emitted from the first energy beam emitter, a second beam emitter/optic sensor pair comprising a second energy beam emitter operable to emit a respective energy beam through a second portion of the off-gas flow at a location spaced downstream from the first portion, and a second optic sensor positioned for receiving and sensing the energy beam emitted from the second energy beam emitter, the first and second optic sensors operable to output electronic signals representative of the sensed energy beam to a processing assembly operable to correlate the electronic signals to an energy absorption signature of said off-gas stream, and wherein said processing assembly is selected to, correlate the electronic signals received from the first optic sensor to identify the energy absorption signatures of off-gas flow at a first position relative to at least part of the said first beam emitter/optic sensor pair, correlate the electronic signals received from said second optic sensor to identify the occurrence of the energy absorption signature at a second position relative to at least part of said second beam emitter/optic sensor pair, and based at least in part on the time between the identification of the energy absorption signature at the first and second positions, provide an output signal based on an identified velocity of at least part of the off-gas flow.

29. The sensor assembly as claimed in claim 28, wherein each energy beam comprises energy having an absorption profile corresponding to an absorption profile of at least one target species component of said gas flow, and said energy absorption signature comprises at least one selected from the group consisting of a total sensed energy beam, a sensed energy corresponding to the absorption profile of the at least one target species, and combinations thereof.

* * * * *